US012692216B2

(12) United States Patent
Guo et al.

(10) Patent No.: US 12,692,216 B2
(45) Date of Patent: Jul. 28, 2026

(54) CONTAMINANT REMOVAL FROM COAL TAR-DERIVED CRUDE PHENOLS

(71) Applicants: UOP LLC, Des Plaines, IL (US); CHINA PETROLEUM & CHEMICAL CORPORATION, Beijing (CN)

(72) Inventors: Liwei Guo, Katy, TX (US); Neelesh Rane, Des Plaines, IL (US)

(73) Assignees: UOP LLC, Des Plaines, IL (US); China Petroleum & Chemical, Beijing (CN)

( * ) Notice: Subject to any disclaimer, the term of this patent is extended or adjusted under 35 U.S.C. 154(b) by 462 days.

(21) Appl. No.: 18/556,919

(22) PCT Filed: May 4, 2021

(86) PCT No.: PCT/US2021/030626
§ 371 (c)(1),
(2) Date: Oct. 24, 2023

(87) PCT Pub. No.: WO2022/235260
PCT Pub. Date: Nov. 10, 2022

(65) Prior Publication Data
US 2024/0182392 A1 Jun. 6, 2024

(51) Int. Cl.
*C07C 37/82* (2006.01)
*C07C 37/00* (2006.01)

(52) U.S. Cl.
CPC ............ *C07C 37/82* (2013.01); *C07C 37/007* (2013.01)

(58) Field of Classification Search
CPC .............................. C07C 37/82; C07C 37/007
See application file for complete search history.

(56) References Cited

U.S. PATENT DOCUMENTS

| | | | |
|---|---|---|---|
| 2,247,523 A | 7/1941 | Schick et al. | |
| 2,606,936 A | 8/1952 | Michael | |
| 2,618,664 A | 11/1952 | Hess et al. | |
| 2,618,665 A | 11/1952 | Hess et al. | |
| 2,618,666 A | 11/1952 | Hess et al. | |
| 2,666,796 A | 1/1954 | Gorin et al. | |
| 2,744,938 A | 5/1956 | Urban, Jr. | |
| 2,766,296 A | 10/1956 | Jones et al. | |
| 2,790,834 A | 4/1957 | Morton et al. | |
| 4,256,568 A | 3/1981 | Schlosberg et al. | |
| 4,595,489 A | 6/1986 | Scouten | |
| 4,827,050 A | 5/1989 | Peter et al. | |
| 4,992,599 A | 2/1991 | Talbiersky et al. | |
| 5,149,887 A * | 9/1992 | Zinnen .................... C07C 37/82 | |
| | | | 568/750 |
| 5,750,009 A | 5/1998 | Duncan et al. | |
| 5,964,987 A | 10/1999 | Duncan et al. | |

| | | | |
|---|---|---|---|
| 7,270,742 B2 | 9/2007 | Karas et al. | |
| 9,162,952 B2 * | 10/2015 | Jan ............................ C10C 1/18 | |
| 2015/0136660 A1 | 5/2015 | Bedard et al. | |

FOREIGN PATENT DOCUMENTS

| | | |
|---|---|---|
| CN | 1105657 A | 7/1995 |
| CN | 1279231 A | 1/2001 |
| CN | 102188962 A | 9/2011 |
| CN | 105198711 A | 12/2015 |
| CN | 105705612 A | 6/2016 |
| CN | 106478379 A | 3/2017 |
| CN | 107721826 A | 2/2018 |
| DE | 1085886 B | 7/1960 |
| GB | 738177 | 10/1955 |
| GB | 992319 | 5/1965 |
| JP | S6212731 A | 1/1987 |
| JP | 2569592 B2 | 3/1989 |
| JP | 6466134 A | 3/1989 |
| JP | S6466134 A | 3/1989 |
| JP | 2006514145 A | 4/2006 |

OTHER PUBLICATIONS

International Preliminary Report on Patentability from corresponding PCT application No. PCT/US2021/030626, mailed Nov. 16, 2023.
International search report and Written Opinion from corresponding PCT application No. PCT/US2021/030626, mailed Jan. 25, 2022.
Charles N. Satterfield et al., Simultaneous Hydrodenitrogenation and Hydrodeoxygenation of Model Compounds in a Trickle Bed Reactor, Journal of Catalysis 81, 335-346 (1983).
Ezekiel O. Odebunmi et al., Catalytic Hydrodeoxygenation, II. Interactions between Catalytic Hydrodeoxygenation of m-Cresol and Hydrodesulfurization of Benzothiophene and Dibenzothiophene, Journal of Catalysis 80, 65-75 (1983).
Zhi-Hao Ma et al., Insight into the Compositions of the Soluble/Insolube Portions from the Acid/Base Extraction of Five Fractions Distilled from a High Temperature Coal Tar, Energy Fuels 2019, 33, 10099-10107.
Tiantian Jiao et al., The new liquid-liquid extraction method for separation of phenolic compounds from coal tar, Chemical Engineering Journal 266 (2015) 148-155.
Jiajun Gao et al., Efficient separation of phenol from oil by acid-base complexing adsorption, Chemical Engineering Journal 281 (2015) 749-758.

* cited by examiner

*Primary Examiner* — Sikarl A Witherspoon
(74) *Attorney, Agent, or Firm* — Greer, Burns & Crain, Ltd.

(57) ABSTRACT

A process for removing contaminants from coal-derived phenols is described. The process combines an extraction process with at least two adsorption zones containing adsorbents. Liquid-liquid and acid base extraction processes can be used. The adsorbents can be clays and/or zeolites. The process can be used to reduce organonitrogen compounds and organosulfur compounds to levels below 10 ppmw and to generate a colorless product.

20 Claims, 6 Drawing Sheets

CONTAMINANT REMOVAL FROM COAL TAR-DERIVED CRUDE PHENOLS

This application is a U.S. National Phase under 35 U.S.C. § 371 of International Application No. PCT/US2021/030626 filed May 4, 2021.

BACKGROUND OF THE INVENTION

Low and medium temperature coal tar contains significant amounts of valuable phenols, especially in the distillation cut below 300° ° C. A phenolic mixture (crude phenols) may be extracted from the distillation cut using various physical and chemical methods, such as extracting with aqueous sodium hydroxide solution followed by neutralization with a strong inorganic acid, selective solvent extraction, ion exchange resin adsorption, etc.

Usually, low and medium temperature coal tars have less than or equal to 1.0% of both nitrogen and sulfur contents. The above-mentioned extraction methods are effective to remove some of the organosulfur and organonitrogen compounds from the crude phenols. Any remaining trace amounts of organosulfur and organonitrogen compounds in the crude phenols must be removed because they act as poisons for catalysts in downstream upgrading processes in which less valuable phenolic compounds are converted into more valuable phenols and aromatics by catalytic dealkylation and transalkylation, for example.

Industrially, hydrotreating is the most commonly applied method for removal of organonitrogen and organosulfur from oils. However, hydrotreating is not a selective process for removing nitrogen and sulfur. In addition to hydrodenitrogenation (HDN) and hydrodesulfurization (HDS), other processes take place in parallel, including hydrodemetalation (HDM), hydrodeoxygenation (HDO), hydrodearomatization (HDA), and olefin saturation. Of the most abundant heteroatoms in oils (S, N, and O), nitrogen is the most difficult to remove by hydroprocessing. In addition, both HDO and HDA destroy phenols. It is recognized that nitrogen is the most difficult to remove and that it is not a good approach to remove N-contaminants from phenols because hydrotreating destroys phenols. "Simultaneous hydrodenitrogenation and hydrodeoxygenation of model compounds in a trickle bed reactor", Journal of Catalysis (1983), 81 (2): 335-346; "Hydrorefining Coal-Tar Naphthalene, Hydrogenolysis over cobalt molybdate catalyst removes impurities containing sulfur, oxygen, and nitrogen and yields a refined product of high purity," Industrial and Engineering Chemistry, Vol. 53, No. 12, 1961, p. 993-6; "Hydrotreatment of model compounds with catalysts of NiW/Al$_2$O$_3$ and NiWP/ Al$_2$O$_3$ to simulate low temperature coal tar oil", RSC Adv., 2017, July, 54512. In addition, sulfur contaminant removal from phenols is not efficient by catalytic hydrodesulfurization (HDS) because HDS is inhibited by phenols like cresol. "Catalytic hydrodeoxygenation: II. Interactions between catalytic hydrodeoxygenation of m-cresol and hydrodesulfurization of benzothiophene and dibenzothiophene", Journal of Catalysis (1983), 80 (1): 65-75.

Other processes have also been used to remove sulfur and/or nitrogen. For example, in GB738177, phenols in coal tar distillate were extracted with an aqueous alkali solution, followed by purifying the resulting phenolate solution by treatment with one or more of the following adsorbing agents: bleaching earth produced from clays of the montmorillonite group (fuller's earth, bentonite, nontronite, beidellite, and hectorite (Mg-bentonite), alumina, a basic oxide, hydroxide or carbonate of either Fe, Mg, or Ca, a "caustic slurry" obtained by heating phenolate lye residue with lime, After neutralization with acids, particularly CO$_2$, phenols were obtained as a clear liquid with acceptable odor. Nitrogen contaminant removal was not addressed.

Another process is described in U.S. Pat. No. 2,247,523. Phenols were extracted from a coal tar distillate into aqueous sodium hydroxide solution. This was followed by treating the resulting phenolate solution with adsorbing agents such as fuller's earth, diatomaceous earth and active carbon. The phenolate solution was treated with an acid, such as HCl, H$_2$SO$_4$, CO$_2$ to release the phenols. The phenols were still colored or at least darken upon standing, especially in the light, and in some cases possessed a disagreeable smell. The smell and the color of the phenols were finally ameliorated by adding a small amount of formaldehyde and by subsequent vacuum distillation. Nitrogen and sulfur contaminant removal was not addressed.

U.S. Pat. No. 2,744,938 described a process for decolorizing an alkyl phenol which has become discolored through oxidation. The process involves contacting a solution of the alkyl phenol in a solvent with an adsorbent selected from the group consisting of activated carbon, alumina, clays, and silica gel at a temperature of from about 40 to about 150° C. in the presence of hydrogen under a super-atmospheric pressure. Nitrogen and sulfur contaminant removal was not addressed.

CN 102188962 disclosed catalysis adsorbents for refining coal-based phenols. The catalysis adsorbent comprises the following active ingredients in percentage by mass: 0 to 99% kaolinite, 15 to 99% active clay, 0 to 20% sepiolite, 0 to 45% diatomite, 0 to 80% mordenite, and 0 to 99% ZSM zeolite. The best result achieved was a reduction of sulfur content from about 1000 ppm to 27 ppm (97.3% S removed). No nitrogen content reduction was mentioned.

Therefore, there is a need for a process to recover crude phenols from coal tar and to remove nitrogen- and sulfur-contaminants from the crude phenols, and which allows the crude phenols to be upgraded efficiently.

DESCRIPTION OF THE INVENTION

Figure 1:
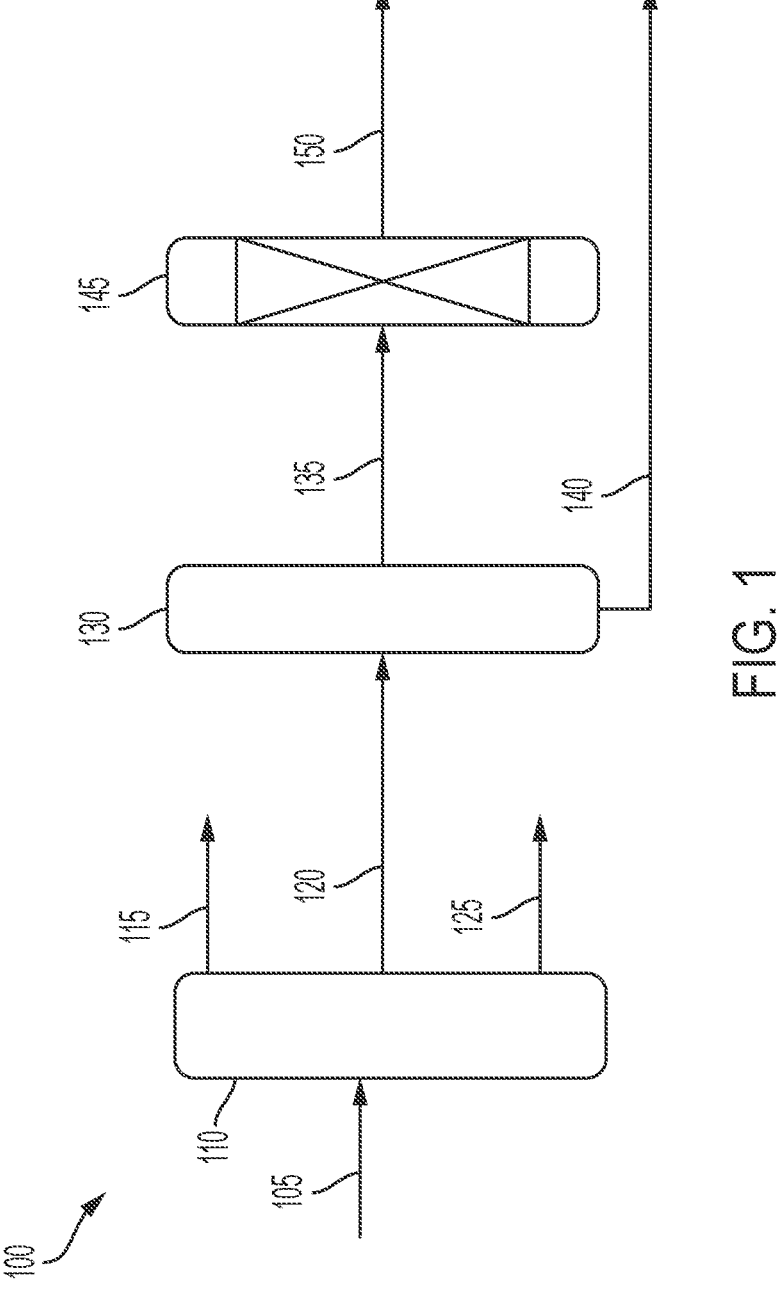
FIG. 1 illustrates one embodiment of the process of the present invention.

The present process provides a method for removing contaminants from coal-derived phenols. Nitrogen compounds are much less reactive than oxygen and sulfur compounds, and they strongly adsorb on the active sites of the catalyst, which hampers the upgrading process of crude phenols.

It has been discovered that a combination of an extraction process followed by an adsorption process allows the preparation of cleaner crude phenols from coal-derived feed streams with levels of sulfur and nitrogen less than 100 ppmw, and less than 10 ppmw in some cases.

Coal-derived feed streams, such as low temperature coal tar, medium temperature coal tar, high temperature coal tar, cresylic acid, or a crude phenolic mixture contain phenol, alkylphenols (methylphenols (cresols), ethylphenols, dimethylphenols(xylenols), propylphenols, butylphenols, methylethylphenols, etc.), as well as heavier alkylphenols (such as indanols and naphthols). Coal tar is derived from the process of dry distillation and gasification of coal and is classified based on the temperature used for this process (400-600° C. (low temperature), 600-1000° C. (medium temperature), and greater than 1000° ° C. (high temperature)). Cresylic acid is a generic term referring to combinations of phenol and alkylphenols, and it can be obtained from either coal or petroleum processing, for example. A crude phenolic mixture can be obtained by the processing of coal tar oils and the purification of phenol containing waste from coke ovens, low temperature carbonization, and hydrogenation plants, for example. The composition of the feed stream will vary depending on its source.

The coal-derived feed stream can be separated into various streams. Suitable separation processes include, but are not limited to, distillation, acid/base extraction, solvent extraction, and the like. The crude phenol stream may comprise a portion of the coal-derived feed stream. The crude phenol stream may comprise a portion of one or more of a low temperature coal tar stream, a medium temperature coal tar stream, a high temperature coal tar stream, a cresylic acid stream, or a crude phenolic mixture. The crude phenol stream may have a boiling point of about 300° C. or less. For example, the crude phenol stream may comprise a portion of a low or medium temperature coal tar distillate stream having a boiling point of about 300° ° C. or less, for example.

The crude phenol stream is subjected to an extraction process to produce an extraction effluent stream with minimal impurities (organonitrogen, organosulfur, and neutral oil), facilitating the subsequent adsorption process. Liquid-liquid extraction methods can be used to separate phenolic compounds from coal tar distillates (for example, about 300° ° C. or less) effectively. Suitable liquid-liquid extraction processes include, but are not limited to, acid-base liquid extraction processes and aqueous methanol liquid extraction processes. It has been determined that the acid/base liquid extraction is more effective for nitrogen and sulfur contaminant removal, although aqueous methanol extraction is safer and easier to operate. Other liquids can be used in the extraction including, but not limited to, ethanol, propanol, glycols, alcohol amines, and the like. In terms of nitrogen and/or sulfur contaminant removal, these two extraction methods are superior to hydrotreating because they do not destroy phenols.

In some embodiments, the acid-base extraction process reduces the organonitrogen in the coal tar distillate stream to below 100 ppmw, and the organosulfur to below 100 ppmw, or 50 ppmw. A coal tar distillate stream or its solution in an aromatic solvent (toluene, benzene, xylene, for examples) is extracted with an aqueous basic solution (3M sodium hydroxide solution, for example) multiple times. The combined extract solutions are then washed with an 80:20 mix of hexane and dichloromethane to remove residual neutral and alkaline coal tar components. After acidification with an acidic solution (Hydrochloric acid, sulfuric acid, for examples), the crude phenol is collected as an oil or extracted with dichloromethane multiple times to improve phenolic recovery. Removal of the solvent yields crude phenol as an oil.

An adsorption process follows the extraction process to remove the remaining traces of refractory nitrogen and sulfur contaminants to obtain the low levels needed for further processing of the stream. It has been discovered that by using more than one adsorbent zone, improved adsorption can be achieved. There can be at least two different adsorbent zones. The first adsorbent zone comprises a clay, and the second adsorbent zone comprises a zeolite. The order of the adsorbent zones is interchangeable.

The adsorption processes can be carried out on a shaker or a column at a temperature in the range of from room temperature to about 90° C., under atmospheric pressure or super-atmospheric pressure, for several hours to several days.

The first adsorbent zone comprises about 20% or more of one or more clays, or about 30% or more, or about 40% or more, or about 50% or more, or about 60% or more, or about 70% or more, or about 80% or more, or about 90% or more, or about 95% or more. Suitable clays include, but are not limited to, bentonite, bentonite-HCl activated, silica gel, sepiolite, and fuller's earth.

The second adsorbent zone comprises about 20% or more of one or more zeolites, or about 30% or more, or about 40% or more, or about 50% or more, or about 60% or more, or about 70% or more, or about 80% or more, or about 90% or more, or about 95% or more. Suitable zeolites include, but are not limited to, HZSM-5 zeolite, and HBETA zeolite.

There can be a third (or more) adsorbent zone comprising a third adsorbent. The third adsorbent can comprise one or more clays and/or one or more zeolites. The third adsorbent zone can comprise a different adsorbent from the first adsorbent and/or the second adsorbent. Alternatively, the third adsorbent can be the same as either the first adsorbent or the second adsorbent. For example, in one embodiment, the clay of the first adsorbent may comprise one or more of bentonite and bentonite-HCl activated; the zeolite of the second adsorbent may comprise one or more of HZSM-5 zeolite and HBETA zeolite; and the third adsorbent may comprise one or more of HZSM-5 zeolite, HBETA zeolite, silica gel, sepiolite, and fuller's earth. In one example, the clay of the first adsorbent comprises bentonite-HCl activated, the zeolite of the second adsorbent comprises HZSM-5 zeolite, and the third adsorbent comprises one or more of fuller's earth or sepiolite.

The designation of first and second (and third or more) adsorbents is merely meant to distinguish them. It is not meant to specify which is first in the process. In other words, the first adsorbent can be upstream of the second adsorbent, or it can be downstream. The third adsorbent can be upstream of both the first and second adsorbent, downstream of both, or in between (with the first adsorbent upstream or downstream of second adsorbent in all cases).

The first and second adsorbent zones can be located in a single vessel, or they can be located in different vessels. When the first and second adsorbent zones are located in the same vessel, the first adsorbent zone may be positioned above the second adsorbent zone, or the second adsorbent zone may be positioned above the first adsorbent zone.

Alternatively, when the first and second adsorbent zones are located in the same vessel, if a third adsorbent zone is present, it can be located in the same vessel as the first adsorbent zone and/or the second adsorbent zone, or in a separate vessel.

Alternatively, there can be one adsorbent zone comprising a mixture of two or more adsorbents, wherein the adsorbents comprise one of clays and zeolites.

The first adsorption zone and/or the second adsorption zone may comprise at least one of fixed bed, a fluidized bed, a moving bed and a rotating bed.

The crude phenol stream may be passed through the adsorbent beds in an upflow or downflow direction.

The extraction effluent stream may have less than 200 ppmw organosulfur compounds, or less than 175 ppmw, or less than 150 ppmw, or less than 125 ppmw, or less than 100 ppmw, or less than 75 ppmw, or less than 50 ppmw. The extraction effluent stream may have less than 1500 ppmw organonitrogen compounds, or less than 1250 ppmw, or less than 1000 ppmw, or less than 750 ppmw, or less than 500 ppmw, or less than 250 ppmw, or less than 100 ppmw. Organosulfur content is measured using an N and S Analyzer: Elementar trace SN cube (available from Elementar Analysensysteme GmbH, Langenselbold, Germany) following ASTM D5453-16 for sulfur analysis. Organonitrogen content is measured using the N and S Analyzer: Elementar trace SN cube, following ASTM D4629-17 for nitrogen analysis.

The adsorption effluent stream may have less than 100 ppmw organosulfur compounds, or less than 75 ppmw, or less than 50 ppmw, or less than 40 ppmw, or less than 30 ppmw, or less than 25 ppmw, or less than 20 ppmw, or less than 15 ppmw, or less than 10 ppmw. The adsorption effluent stream may have less than 100 ppmw organonitrogen compounds, or less than 75 ppmw, or less than 50 ppmw, or less than 40 ppmw, or less than 30 ppmw, or less than 25 ppmw, or less than 20 ppmw, or less than 15 ppmw, or less than 10 ppmw. The presence of color in the crude phenol stream is a sign of nitrogen and/or sulfur contamination in the crude phenol because the phenolic compounds themselves are colorless. The adsorption effluent stream may be colorless using a visual determination, demonstrating that the level of organonitrogen and/or organosulfur compounds has been reduced.

An adsorption process (following extraction) in which the first adsorbent was bentonite-HCl activated, the second adsorbent was H-ZSM5, and the third adsorbent was Fuller's earth generated a colorless adsorbent effluent stream. In contrast, the same three adsorbents in a single mixed bed did not eliminate the color in the adsorbent effluent stream completely. However, there may be downstream processes in which this level of nitrogen and sulfur contaminants is acceptable.

The process may provide a phenolic recovery rate of 75% or more, or 80% or more, or 85% or more, or 90% or more, or 92% or more, or 93% or more, or 94% or more, or 95% or more. This may be compared with the hydrotreating process in which greater than 90% of the phenolics are destroyed.

The phenolic recovery rate is calculated by the formula:

$$\left[\frac{(\text{Amt of phenolics in adsorption effluent})}{\text{Amt of phenolics in extraction effluent}} \times 100\%\right]$$

For example, there were no obvious compositional changes after a 3-zone adsorption process with Bentonite-HCl/H-ZSM5/Fuller's earth. GC-MS analyses were applied to determine changes in the phenolic composition before and after the adsorption processes.

FIG. 1 illustrates the process 100. The coal tar or crude phenol feed stream 105 is separated in one or more distillation columns 110 into one or more streams. For example, the coal tar or crude phenol feed stream 105 may divided into stream 115 with a boiling point of less than about 150° C., crude phenol stream 120 with a boiling point of about 150° C. to about 300° C., and stream 125 with a boiling point of greater than 300° C. Those of skill in the art will know that other splits in the coal tar or crude phenol feed stream 105 are possible.

Crude phenol stream 120 contains most of the phenolic compounds in the coal tar or crude phenol feed stream 105. It is sent to one or more extraction columns 130. A portion of the organosulfur and organonitrogen compounds are removed from crude phenol stream 120 resulting in an extraction effluent stream 135 having a reduced level of organosulfur and organonitrogen compounds compared to incoming crude phenol stream 120 and stream 140 containing oil with a reduced level of phenols and the organosulfur and organonitrogen compounds removed from crude phenol stream 120. The extraction process can be an acid-base liquid extraction process or an aqueous methanol liquid extraction process.

The extraction effluent stream 135 is sent to an adsorption unit 145 comprising first and second adsorption zones containing first and second adsorbents. The adsorption unit 145 can include one or more adsorption vessels, each containing one or more adsorption zones, as is known in the art. The adsorption unit may include three or more adsorption zones as described above. An additional portion of the organosulfur and organonitrogen compounds are removed from the extraction effluent stream 135 in the adsorption unit 145 resulting in an adsorption effluent stream 150 having a reduced level of organosulfur and organonitrogen compounds compared to the incoming extraction effluent stream 135.

The adsorption effluent stream 150 can be sent to downstream phenolic separation and/or further processing.

The selection of adsorbents in combination is based on the findings from an adsorbent selectivity investigation for coal tar. Adsorption was measured using gas chromatography-nitrogen chemiluminescence detector (GC-NCD). NCD is a nitrogen-specific detection tool, which is very sensitive and useful for detection of residual nitrogen contaminants in coal tar samples because only N-containing compounds appear in the chromatogram.

It was discovered that a single adsorbent was not efficient enough to reduce contaminants to the desired level. However, when an extraction effluent was subjected to a different single adsorbent in parallel under the same experimental conditions, comparison of the resulting GC-NCD chromatograms provided valuable information on the nitrogen contaminant adsorption selectivity of these adsorbents.

Figures 2, 3A:
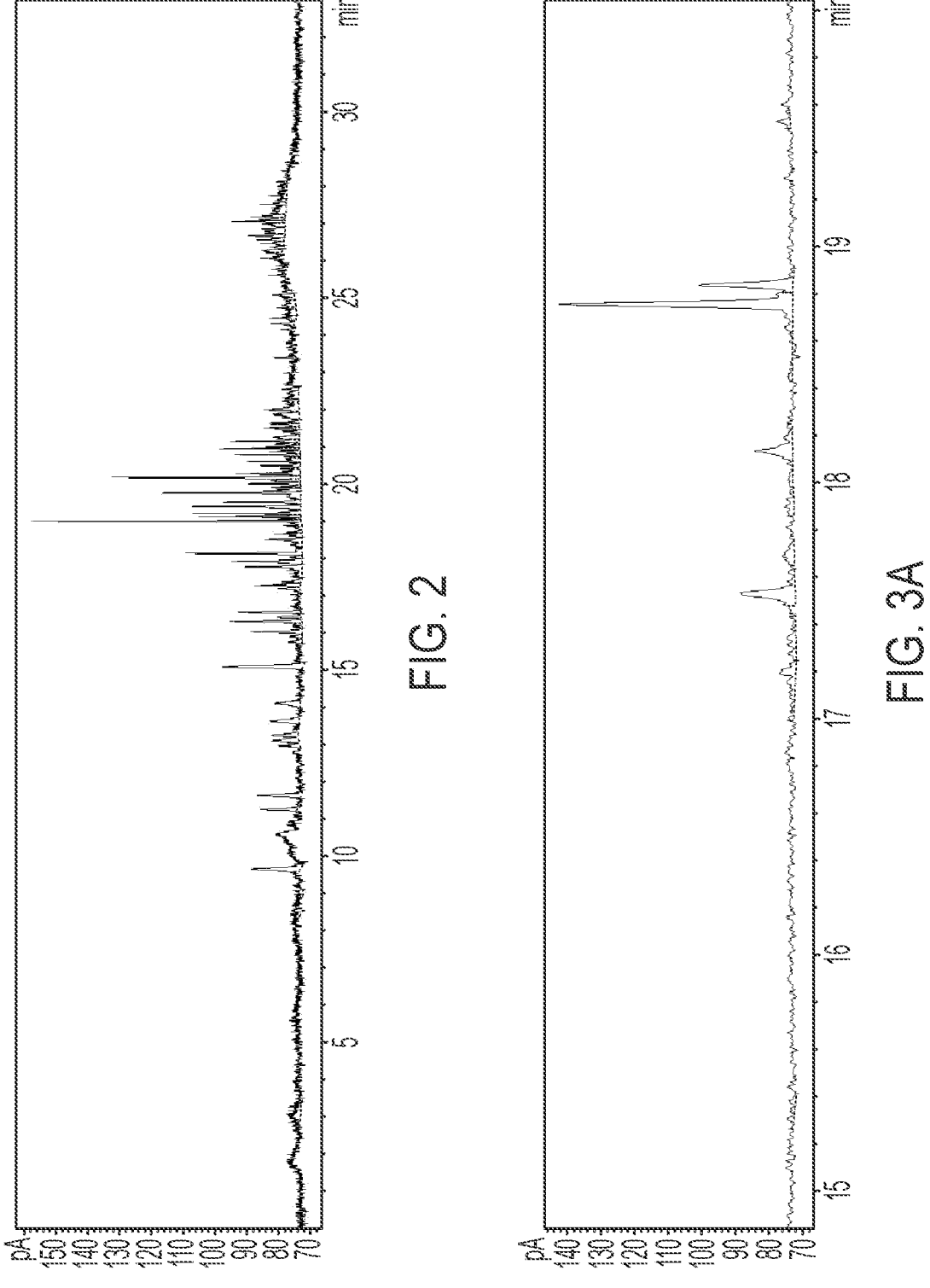
FIG. 2 is a GC-NCD chromatogram of Sample 1 prior to adsorption.
FIG. 3A is GC-NCD chromatogram of Sample 1 after adsorption using bentonite-HCl.

For example, FIG. 2 shows the GC-NCD chromatogram of Sample 1, which is the effluent from an acid-base extraction process, prior to adsorption.

Figures 3B, 4A:
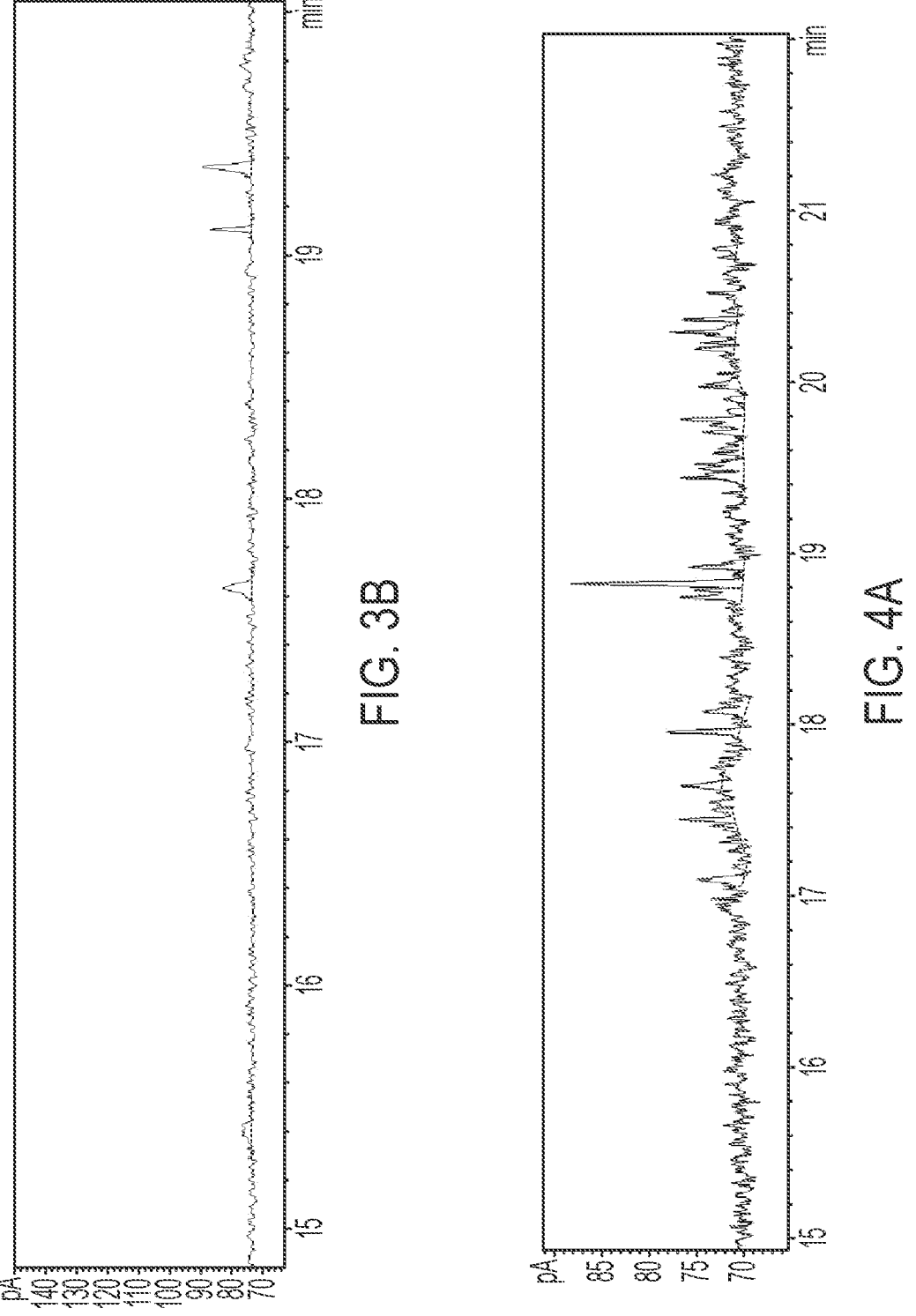
FIG. 3B is GC-NCD chromatogram of Sample 1 after adsorption using HZSM-5 zeolite.
FIG. 4A is GC-NCD chromatogram of Sample 1 after adsorption using sepiolite.

FIGS. 3A and 3B show the GC-NCD chromatograms of Sample 1 after adsorption using bentonite-HCl (same material as in FIGS. 5B and 6B, but the scale is different) and HZSM-5 zeolite (same material as in FIG. 4B, but the scale is different) respectively. As can be seen, the remaining peaks are different which means that the two adsorbents adsorb different nitrogen molecules.

Figures 4B, 5A:
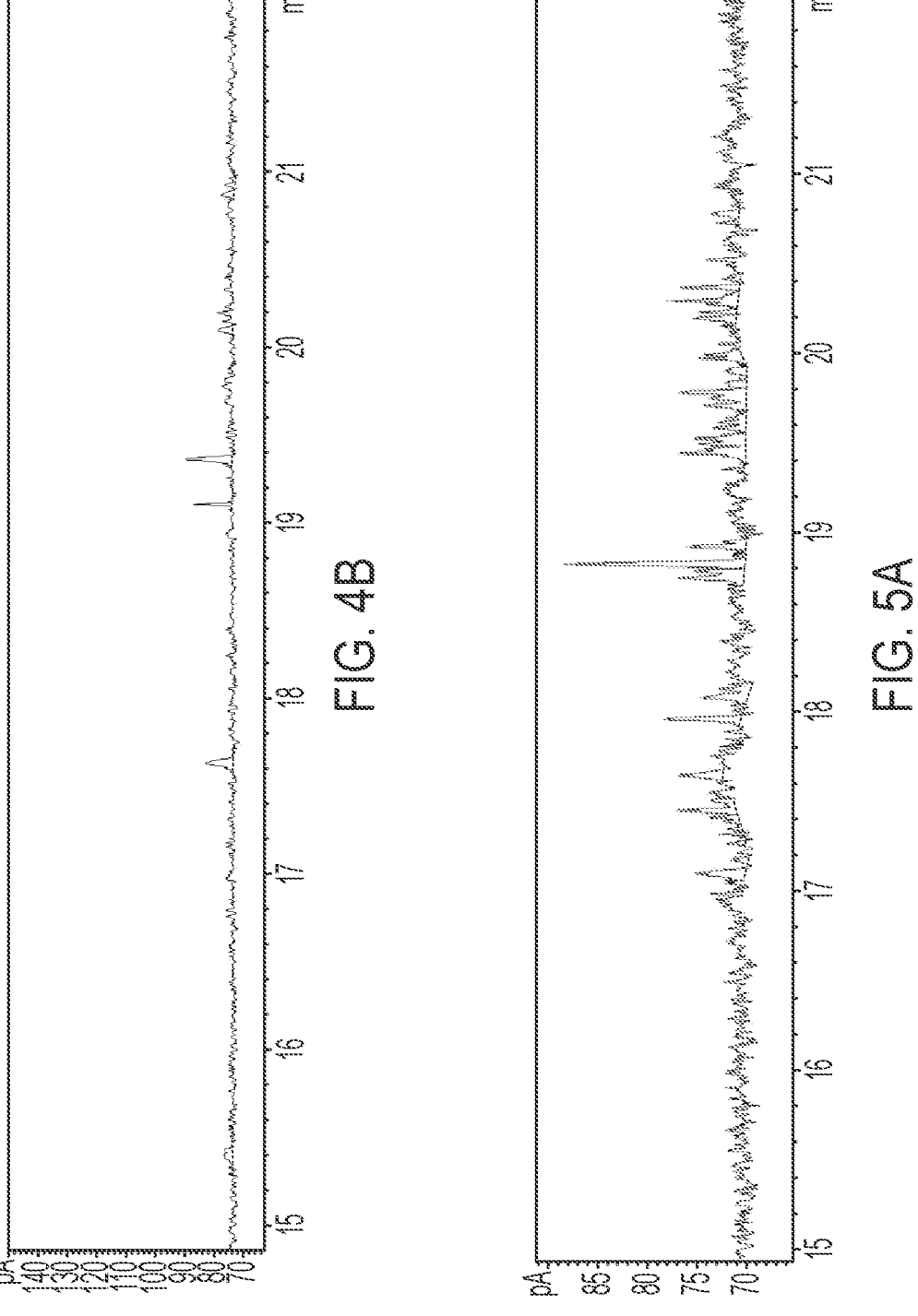
FIG. 4B is GC-NCD chromatogram of Sample 1 after adsorption using HZSM-5.
FIG. 5A is GC-NCD chromatogram of Sample 1 after adsorption using sepiolite.

FIGS. 4A and 4B show the GC-NCD chromatograms of Sample 1 after adsorption using sepiolite (same material as in FIG. 5A with the same scale) and HZSM-5 zeolite (same material as in FIG. 3B, but the scale is different) respectively. The remaining peaks are different for the two adsorbents indicating that they adsorb different nitrogen molecules.

Figures 5B, 6A:
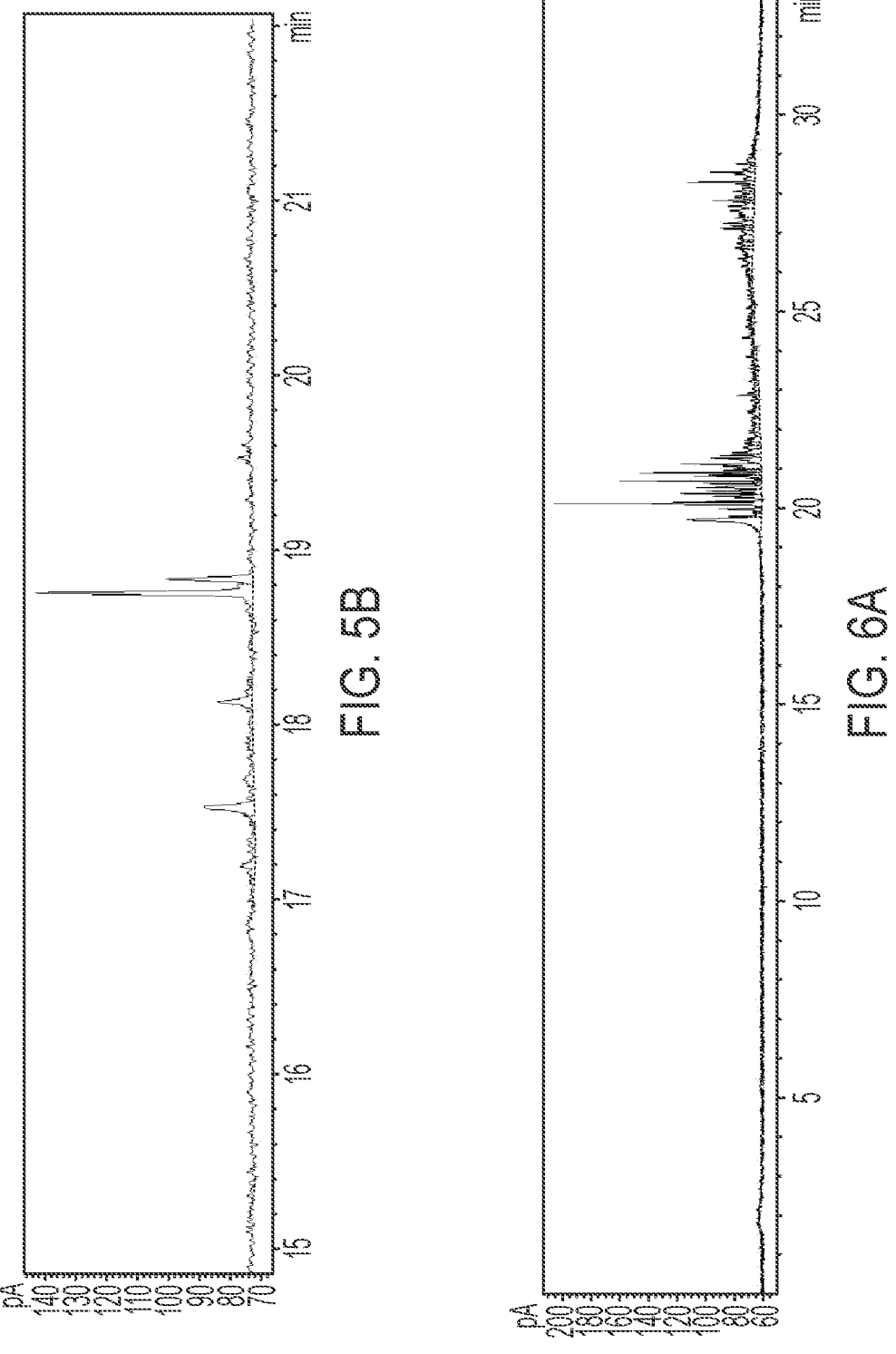
FIG. 5B is GC-NCD chromatogram of Sample 1 after adsorption using bentonite-HCl.
FIG. 6A is GC-NCD chromatogram of Sample 1 after adsorption using fuller's earth.

FIGS. 5A and 5B show the GC-NCD chromatograms of Sample 1 after adsorption using sepiolite (same material as in FIG. 4A with the same scale) and bentonite-HCl (same material as in FIGS. 3A and 6B, but the scale is different) respectively. The differences in the remaining peaks mean that they adsorb different nitrogen molecules.

Figure 6B:
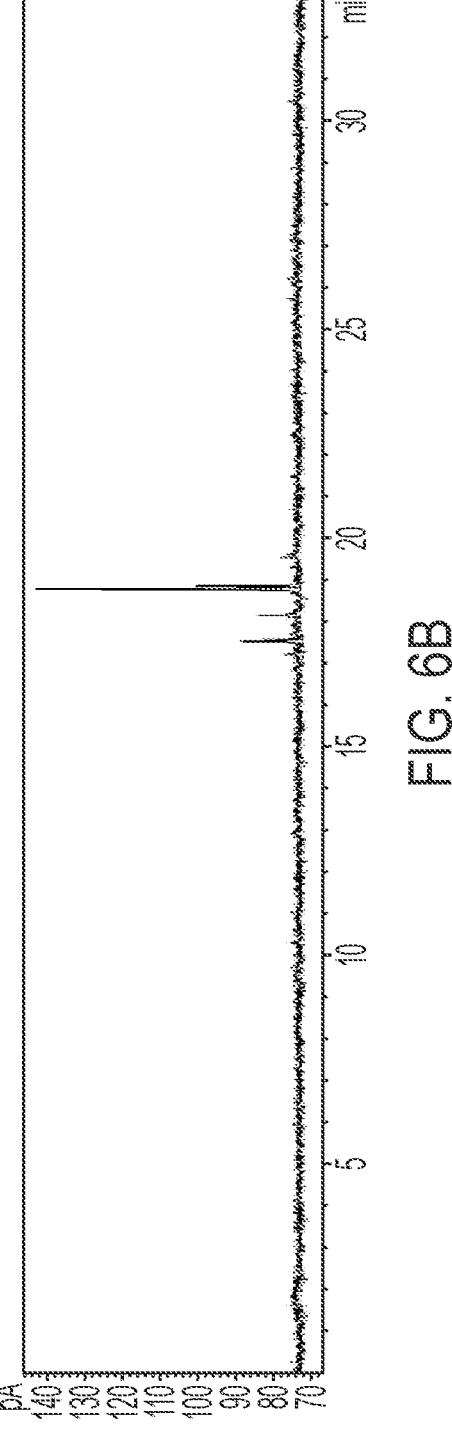
FIG. 6B is GC-NCD chromatogram of Sample 1 after adsorption using bentonite-HCl.

FIGS. 6A and 6B show the GC-NCD chromatograms of Sample 1 after adsorption using fuller's earth and bentonite-HCl (same material as in FIGS. 3A and 5B, but the scale is different) respectively. The differences in the remaining peaks mean that they adsorb different nitrogen molecules.

Experiments with the effluent from an aqueous methanol extraction process yielded similar results, i.e., different adsorbents adsorbed different nitrogen molecules.

The adsorbent selectivity investigations demonstrated that different adsorbents adsorbed different nitrogen compounds from the extraction effluents. Thus, it was shown that the performances of the adsorbents are complementary in nitrogen contaminant removal, and the adsorbents will generate synergistic effects when used in combination.

From this, it would be expected that different adsorbents would adsorb different sulfur molecules.

Although the process is described below for use with coal tar for the sake of convenience, those of skill in the art will recognize that it can also be used for other coal derived liquids, including, but not limited to, the liquid generated by the coal liquefaction process.

EXAMPLES

Example 1—Extraction Process

A part of a coal tar distillation cut (150-250° C., the initial N level 4200 ppmw and S level 700 ppmw) was subjected to an acid/base extraction process. The distillation cut (2.3 kg) was dissolved in 5.6 kg of toluene. The resulting solution in toluene was extracted with 3.0 M aqueous NaOH solution three times (first 8.6 kg, second 6.3 kg, third 4.0 kg) at room temperature. The combined aqueous phases were extracted with hexane/dichloromethane (4:1 v/v) twice (2.6 kg each) to remove residual neutral and alkaline components. 6 M hydrochloric acid (9.5 kg) was slowly added to the aqueous phase at 10° C. under stirring to acidify to pH 1.0. The acidified aqueous phase was extracted with dichloromethane three times (5.3 kg each). The combined dichloromethane solutions were washed with distilled (DI) water two times (0.5 L each) to remove residual salts. Dichloromethane and residual water were removed by rotary evaporation yielding the crude phenol stream (1.25 kg, a yield of 55 wt %).

The effluent from the acid/base extraction process had 96 ppmw nitrogen and 47 ppmw sulfur (Sample 1).

Another part of the same distillation cut was subjected to an aqueous methanol extraction process. The distillation cut (1.0 kg) was dissolved in 4.0 L of methanol, followed by addition of 1.7 L of DI water. The volumetric ratio of methanol and water is 70:30. A cloudy mixture resulted because less polar components (non-phenolic compounds) became insoluble. The cloudy mixture in the aqueous methanol was extract with hexane three times (1.0 L each time). The methanol and water were removed by rotary evaporation yielded a crude phenol oil, which was further subjected to extraction with 1.0 M hydrochloric acid two times (200 mL each) to remove the alkaline organonitrogen compounds. After removal of residual water by rotary evaporation at 50° ° C. in vacuum (10 mmHg) for 4 hours, a crude phenol stream (0.56 kg, a yield of 52 wt %) was obtained.

The effluent from the aqueous methanol extraction process had a 1468 ppmw nitrogen and 174 ppmw sulfur (Sample 2).

Example 2—Adsorption Process

Samples 1 and 2 were then subjected to adsorption using a variety of adsorbents.

Pretreatment of Adsorbents:

Acid-Activated Bentonite (Bentonite-HCl):

To 40.0 g of bentonite clay was added 80 mL of 3.0 M hydrochloric acid (HCl). The resulting mixture was heated at 70° C. for 12 hours with mild agitation. After filtration, the collected solid was dried at 105° C. for 12 hours. The dried HCl-treated bentonite was crushed and sized to 30-50 mesh before use. The dried bentonite was stored under nitrogen.

Zeolite adsorbents (HZSM-5, HBETA, etc.) were sized (30-50 mesh) and calcined at 540° ° C. for 3 hrs. All other adsorbents were pretreated at 150° C. for 1 hr to remove adsorbed compounds before use.

Adsorption Process 1: Sample 1 (10.0 g) was dissolved in 30.0 g of toluene, followed by addition of 5.0 g of bentonite-HCl. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent sepiolite was added. The resulting mixture was allowed to shake for 2-24 hrs. After filtration to remove the third adsorbent and removal of solvent, a colorless oil was obtained with N and S levels at 5 ppmw and 6 ppmw, respectively.

Adsorption Process 2: Sample 1 (10.0 g) was dissolved in 30.0 g of toluene, followed by addition of 5.0 g of bentonite-HCl. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent fuller's earth was added. The resulting mixture was allowed to shake for 2-24 hrs. After filtration to remove the third adsorbent and removal of solvent, a colorless oil was obtained with N and S levels at 8 ppmw and 6 ppmw, respectively. The phenolic recovery is 93%.

Adsorption Process 3: Sample 1 (10.0 g) was dissolved in 30.0 g of toluene, followed by addition of a mix of bentonite-HCl, HZSM-5 (Zeolyst, CBV3024E), and fuller's earth (5 g each). The resulting mixture was allowed to shake for 2-24 hrs. After filtration to remove the adsorbent mix and removal of solvent, a pale brown oil was obtained with N and S levels at 42 ppmw and 10 ppmw, respectively. The phenolic recovery is 92%.

Adsorption Process 4: Sample 1 (10.0 g) was dissolved in 30.0 g of toluene, followed by addition of 5.0 g of bentonite-HCl. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent HBETA (Clariant, HCZB150) was added. The resulting mixture was allowed to shake for 2-24 hrs. After filtration to remove the third adsorbent and removal of solvent, a pale yellow oil was obtained with N and S levels at 18 ppmw and 9 ppmw, respectively.

Adsorption Process 5: Sample 1 (10.0 g) was dissolved in 30.0 g of toluene, followed by addition of 5.0 g of bentonite-HCl. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent and removal of solvent, a pale brown oil was obtained with N and S levels at 29 ppmw and 15 ppmw, respectively. The phenolic recovery is 95%.

Adsorption Process 6: Sample 1 (10.0 g) was dissolved in 30.0 g of toluene, followed by addition of 5.0 g of bentonite. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent and removal of solvent, a pale brown oil was obtained with N and S levels at 62 ppmw and 22 ppmw, respectively.

Adsorption Process 7: Sample 1 (10.0 g) was dissolved in 30.0 g of toluene, followed by addition of 5.0 g of bentonite. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent silica gel was added. The resulting mixture was allowed to shake for 2-24 hrs. After filtration to remove the third adsorbent and removal of solvent, a pale brown oil was obtained with N and S levels at 42 ppmw and 12 ppmw, respectively.

Adsorption Process 8: Sample 1 (10.0 g) was dissolved in 30.0 g of toluene, followed by addition of 5.0 g of bentonite. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent silica gel was added. The resulting mixture was allowed to shake for 2-24 hrs. After filtration to remove the third adsorbent, 5.0 g of a fourth adsorbent fuller's earth was added. The resulting mixture was allowed to shake for 2-24 hrs. After filtration and removal of solvent, a colorless oil was obtained with N and S levels at 15 ppmw and 4 ppmw, respectively. The phenolic recovery rate is 93%.

Adsorption Process 9: Sample 1 (10.0 g) was dissolved in 30.0 g of toluene, followed by addition of 5.0 g of bentonite. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent HBETA (Clariant, HCZB150) was added. The resulting mixture was allowed to shake for 2-24 hrs. After filtration to remove the third adsorbent and removal of solvent, a pale brown oil was obtained with N and S levels at 26 ppmw and 9 ppmw, respectively.

Adsorption Process 10: Sample 1 (10.0 g) was dissolved in 30.0 g of toluene, followed by addition of 5.0 g of bentonite. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent HBETA (Clariant, HCZB150) was added.

The resulting mixture was allowed to shake for 2-24 hrs. After filtration to remove the third adsorbent, 5.0 g of a fourth adsorbent fuller's earth was added. The resulting mixture was allowed to shake for 2-24 hrs. After filtration and removal of solvent, a colorless oil was obtained with N and S levels at 17 ppmw and 5 ppmw, respectively.

Adsorption Process 11: Sample 2 (10.0 g) was dissolved in 30.0 g of toluene, followed by addition of 5.0 g of bentonite-HCl. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent silica gel was added. The resulting mixture was allowed to shake for 2-24 hrs. After filtration to remove the third adsorbent and removal of solvent, a brown oil was obtained with N and S levels at 403 ppmw and 96 ppmw, respectively.

Adsorption Process 12: Sample 2 (10.0 g) was dissolved in 30.0 g of toluene, followed by addition of 5.0 g of bentonite-HCl. The resulting mixture was allowed to shake for 2-24 hrs. After filtration to remove the first adsorbent, 5.0 g of a second adsorbent HZSM-5 (Zeolyst, CBV3024E) was added. The resulting mixture was allowed to shake for 2-24 hrs. After filtration to remove the second adsorbent, 5.0 g of a third adsorbent silica gel was added. The resulting mixture was allowed to shake for 2-24 hrs. After filtration to remove the third adsorbent, 5.0 g of a fourth adsorbent HBETA (Clariant, HCZB150) was added. The resulting mixture was allowed to shake for 2-24 hrs. After filtration and removal of solvent, a brown oil was obtained with N and S levels at 299 ppmw and 59 ppmw, respectively.

TABLE 1

| Adsorption Feed from Acid-base Extraction (Sample 1) (N 96 ppmw, S 47 ppmw) | | |
| --- | --- | --- |
| Adsorption Process | Effluent N ppmw | Effluent S ppmw | Phenolic Recovery, % |
| 1 | 5 | 6 | |
| 2 | 8 | 6 | 93 |
| 3 | 42 | 10 | 92 |
| 4 | 18 | 9 | |
| 5 | 29 | 15 | 95 |
| 6 | 62 | 22 | |
| 7 | 42 | 12 | |
| 8 | 15 | 4 | 93 |
| 9 | 26 | 9 | |
| 10 | 17 | 5 | |

TABLE 2

| Adsorption Feed from 70% Aqueous Methanol Extraction (Sample 2) (N 1468 ppmw, S 174 ppmw) | | |
| --- | --- | --- |
| Adsorption Process | Effluent N ppmw | Effluent S ppmw | Phenolic Recovery, % |
| 11 | 403 | 96 | |
| 12 | 299 | 59 | |

Although the acid/base extraction process and the 70% aqueous methanol extraction process are comparable in phenols extraction from coal tar, the acid/base extraction process is greatly superior to the aqueous methanol extraction process in terms of nitrogen and sulfur contaminant removal efficiency.

The best adsorbent combinations for nitrogen and sulfur contaminant removal efficiency were Bentonite-HCl/HZSM-5/fuller earth and Bentonite-HCl/HZSM-5/sepiolite. Both combinations reduced the nitrogen and sulfur contaminant levels to below 10 ppm.

The term "about" means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of removing contaminants from coal-derived crude phenols comprising;

removing organosulfur compounds and organonitrogen compounds from a crude phenol stream comprising coal-derived crude phenols using an extraction process to form an extraction effluent stream having a reduced level of one or more of the organosulfur compounds and the organonitrogen compounds compared to the crude phenol stream; and removing a portion of one or more of the organosulfur compounds and the organonitrogen compounds from the extraction effluent stream using an adsorption process comprising a first adsorption zone having a first adsorbent and a second adsorption zone having a second adsorbent to form an adsorption effluent stream having a reduced level of one or more of the organosulfur compounds and the organonitrogen compounds compared to the extraction effluent stream, wherein the first adsorbent comprises a clay and wherein the second adsorbent comprises a zeolite.

2. The method of claim 1 wherein the reduced level of the organosulfur compounds in the extraction effluent stream is less than 100 ppmw; or wherein the reduced level of the organonitrogen compounds in the extraction effluent stream is less than 100 ppmw; or both.

3. The method of claim 1 wherein the reduced level of the organosulfur compounds in the adsorption effluent stream is less than 10 ppmw; or wherein the reduced level of the organonitrogen compounds in the adsorption effluent stream is less than 10 ppmw; or both.

4. The method of claim 1 wherein a phenolic recovery rate is 90% or more.

5. The method of claim 1 wherein the extraction process comprises an acid-base liquid extraction process or an aqueous methanol liquid extraction process.

6. The method of claim 1 wherein the clay comprises one or more of bentonite and bentonite-HCl activated.

7. The method of claim 1 wherein the zeolite comprises one or more of HZSM-5 zeolite, and HBETA zeolite.

8. The method of claim 1 wherein the adsorption process further comprises a third adsorption zone comprising a third adsorbent.

9. The method of claim 8 wherein the third adsorbent is different from the first adsorbent and the second adsorbent.

10. The method of claim 8 wherein the clay of the first adsorbent comprises one or more of bentonite, and bentonite-HCl activated, wherein the zeolite of the second adsorbent comprises one or more of HZSM-5 zeolite, and HBETA zeolite, and wherein the third adsorbent comprises one or more of HZSM-5 zeolite, HBETA zeolite, silica gel, sepiolite, and fuller's earth.

11. The method of claim 1 wherein the adsorption process further comprises a third adsorption zone having a third adsorbent, and wherein the first adsorbent comprises bentonite-HCl activated, the second adsorbent comprises HZSM-5 zeolite, and the third adsorbent comprises one or more of fuller's earth or sepiolite.

12. The method of claim 1 wherein the first adsorbent zone and the second adsorbent zone are in separate vessels.

13. The method of claim 1 wherein the first adsorbent zone and the second adsorbent zone are in one vessel wherein the first adsorbent zone is positioned above the second adsorbent zone or wherein the second adsorbent zone is positioned above the first adsorbent zone.

14. The method of claim 1 wherein the crude phenol stream is passed through the adsorbent beds in an upflow or downflow direction.

15. The method of claim 1 wherein the adsorption effluent stream is colorless.

16. The method of claim 1 wherein the crude phenol stream comprises a portion of a coal-derived feed stream, the portion having a boiling point of about 300° C. or less.

17. The method of claim 1 wherein the crude phenol stream comprises a portion of one or more of a low temperature coal tar stream, a medium temperature coal tar stream, a high temperature coal tar stream, a cresylic acid stream, or a crude phenolic mixture.

18. The method of claim 1 wherein at least one of the first adsorption zone and the second adsorption zone comprise at least one of a fixed bed, a fluidized bed, a moving bed, and a rotating bed.

19. A method of removing contaminants from coal-derived crude phenols comprising;

removing organosulfur compounds and organonitrogen compounds from a crude phenol stream comprising coal-derived crude phenols using an extraction process to form an extraction effluent stream having a reduced level of one or more of the organosulfur compounds and the organonitrogen compounds compared to the crude phenol stream, wherein the extraction process comprises one or more of an acid-base liquid extraction process, and an aqueous methanol liquid extraction process; and removing a portion of one or more of the organosulfur compounds and the organonitrogen compounds from the extraction effluent stream using an adsorption process comprising a first adsorption zone having a first adsorbent and a second adsorption zone having a second adsorbent to form an adsorption effluent stream having a reduced level of one or more of the organosulfur compounds and the organonitrogen compounds compared to the extraction effluent stream, wherein the first adsorbent comprises one or more of bentonite, bentonite-HCl activated, silica gel, sepiolite, and fuller's earth, and wherein the second adsorbent comprises HZSM-5 zeolite, and HBETA zeolite.

20. A method of removing contaminants from coal-derived crude phenols comprising;

removing organosulfur compounds and organonitrogen compounds from a crude phenol stream comprising coal-derived crude phenols using an extraction process to form an extraction effluent stream having a reduced level of one or more of the organosulfur compounds and the organonitrogen compounds compared to the crude phenol stream; and removing a portion of one or more of the organosulfur 5 compounds and the organonitrogen compounds from the extraction effluent stream using an adsorption process comprising at least one adsorption zone having an adsorbent to form an adsorption effluent stream having a reduced level of one or more of the organosulfur 10 compounds and the organonitrogen compounds compared to the extraction effluent stream, wherein the adsorbent comprises a mixture of one or more of bentonite, bentonite-HCl activated, silica gel, sepiolite, and fuller's earth and one or more of HZSM-5 zeolite, 15 and HBETA zeolite.

\* \* \* \* \*